United States Patent
Bresnick

(10) Patent No.: US 8,541,181 B2
(45) Date of Patent: Sep. 24, 2013

(54) MYOSIN-IIA S1943 PHOSPHORYLATION AS A MARKER OF TUMOR INVASION

(75) Inventor: Anne Reba Bresnick, Pelham, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 13/419,805

(22) Filed: Mar. 14, 2012

(65) Prior Publication Data
US 2012/0237952 A1      Sep. 20, 2012

Related U.S. Application Data

(60) Provisional application No. 61/453,336, filed on Mar. 16, 2011.

(51) Int. Cl.
*G01N 33/574* (2006.01)
(52) U.S. Cl.
USPC .......................................... 435/7.1; 435/7.23
(58) Field of Classification Search
None
See application file for complete search history.

(56) References Cited

PUBLICATIONS

Dulyaninova et al, Mole Biology of the Cell, 18:3144-3155, 2007, May 29, 2012.*
Norwood et al Mol Bio Cell 21:4299, Dec. 2010, abstract, May 29, 2012.*
Wang, W., Wyckoff, J. B., Goswami, S., Wang, Y., Sidani, M., Segall, J. E., and Condeelis, J. S. (2007) Coordinated regulation of pathways for enhanced cell motility and chemotaxis is conserved in rat and mouse mammary tumors, Cancer Res 67, 3505-3511.
Wyckoff, J. B., Pinner, S. E., Gschmeissner, S., Condeelis, J. S., and Sahai, E. (2006) ROCK- and myosin-dependent matrix deformation enables protease-independent tumor-cell invasion in vivo, Curr Biol 16, 1515-1523.
Dulyaninova, N. G., House, R. P., Betapudi, V., and Bresnick, A. R. (2007) Myosin-IIA heavy-chain phosphorylation regulates the motility of MDA-MB-231 carcinoma cells., Mol Biol Cell 18, 3144-3155.
Beach, JR et al., Myosin II isoform switching mediates invasiveness after TGF-β-induced epithelial-mesenchymal transition, Proc Natl Acad Sci U S A. Nov. 1, 2011;108(44):17991-6. Epub Oct. 24, 2011.
Norwood et al., Myosin-IIA Heavy Chain Phosphorylation Is Associated with Tumor Cell Invasion. Molecular Biology of the Cell, vol. 21, 4299-4299, Dec. 15, 2010, Abstract 180/B256.

* cited by examiner

*Primary Examiner* — Lei Yao
(74) *Attorney, Agent, or Firm* — Amster, Rothstein & Ebenstein LLP

(57) ABSTRACT

Methods and kits are provided for determining if cells of a tumor in an organ or a tissue in a subject are likely to invade another organ or tissue in the subject and for determining if a cancer in a subject is likely to metastasize.

9 Claims, 5 Drawing Sheets

SEQUENCE LISTING

```
<160> NUMBER OF SEQ ID NOS: 1

<210> SEQ ID NO 1
<211> LENGTH: 1960
<212> TYPE: PRT
<213> ORGANISM: Homo Sapiens

<400> SEQUENCE: 1

Met Ala Gln Gln Ala Ala Asp Lys Tyr Leu Tyr Val Asp Lys Asn Phe
1               5                   10                  15

Ile Asn Asn Pro Leu Ala Gln Ala Asp Trp Ala Ala Lys Lys Leu Val
            20                  25                  30

Trp Val Pro Ser Asp Lys Ser Gly Phe Glu Pro Ala Ser Leu Lys Glu
        35                  40                  45
```

-continued

```
Glu Val Gly Glu Glu Ala Ile Val Glu Leu Val Glu Asn Gly Lys Lys
    50                  55                  60

Val Lys Val Asn Lys Asp Ile Gln Lys Met Asn Pro Pro Lys Phe
65                  70                  75                  80

Ser Lys Val Glu Asp Met Ala Glu Leu Thr Cys Leu Asn Glu Ala Ser
                85                  90                  95

Val Leu His Asn Leu Lys Glu Arg Tyr Tyr Ser Gly Leu Ile Tyr Thr
            100                 105                 110

Tyr Ser Gly Leu Phe Cys Val Ile Asn Pro Tyr Lys Asn Leu Pro
        115                 120                 125

Ile Tyr Ser Glu Glu Ile Val Glu Met Tyr Lys Gly Lys Lys Arg His
    130                 135                 140

Glu Met Pro Pro His Ile Tyr Ala Ile Thr Asp Thr Ala Tyr Arg Ser
145                 150                 155                 160

Met Met Gln Asp Arg Glu Asp Gln Ser Ile Leu Cys Thr Gly Glu Ser
                165                 170                 175

Gly Ala Gly Lys Thr Glu Asn Thr Lys Lys Val Ile Gln Tyr Leu Ala
            180                 185                 190

Tyr Val Ala Ser Ser His Lys Ser Lys Asp Gln Gly Glu Leu Glu
        195                 200                 205

Arg Gln Leu Leu Gln Ala Asn Pro Ile Leu Glu Ala Phe Gly Asn Ala
    210                 215                 220

Lys Thr Val Lys Asn Asp Asn Ser Ser Arg Phe Gly Lys Phe Ile Arg
225                 230                 235                 240

Ile Asn Phe Asp Val Asn Gly Tyr Ile Val Gly Ala Asn Ile Glu Thr
                245                 250                 255

Tyr Leu Leu Glu Lys Ser Arg Ala Ile Arg Gln Ala Lys Glu Glu Arg
            260                 265                 270

Thr Phe His Ile Phe Tyr Tyr Leu Leu Ser Gly Ala Gly Glu His Leu
        275                 280                 285

Lys Thr Asp Leu Leu Leu Glu Pro Tyr Asn Lys Tyr Arg Phe Leu Ser
    290                 295                 300

Asn Gly His Val Thr Ile Pro Gly Gln Gln Asp Lys Asp Met Phe Gln
305                 310                 315                 320

Glu Thr Met Glu Ala Met Arg Ile Met Gly Ile Pro Glu Glu Gln
                325                 330                 335

Met Gly Leu Leu Arg Val Ile Ser Gly Val Leu Gln Leu Gly Asn Ile
            340                 345                 350

Val Phe Lys Lys Glu Arg Asn Thr Asp Gln Ala Ser Met Pro Asp Asn
        355                 360                 365

Thr Ala Ala Gln Lys Val Ser His Leu Leu Gly Ile Asn Val Thr Asp
    370                 375                 380

Phe Thr Arg Gly Ile Leu Thr Pro Arg Ile Lys Val Gly Arg Asp Tyr
385                 390                 395                 400

Val Gln Lys Ala Gln Thr Lys Glu Gln Ala Asp Phe Ala Ile Glu Ala
                405                 410                 415

Leu Ala Lys Ala Thr Tyr Glu Arg Met Phe Arg Trp Leu Val Leu Arg
            420                 425                 430

Ile Asn Lys Ala Leu Asp Lys Thr Lys Arg Gln Gly Ala Ser Phe Ile
        435                 440                 445

Gly Ile Leu Asp Ile Ala Gly Phe Glu Ile Phe Asp Leu Asn Ser Phe
    450                 455                 460

Glu Gln Leu Cys Ile Asn Tyr Thr Asn Glu Lys Leu Gln Gln Leu Phe
465                 470                 475                 480
```

-continued

```
Asn His Thr Met Phe Ile Leu Glu Gln Glu Tyr Gln Arg Glu Gly
                485                 490                 495

Ile Glu Trp Asn Phe Ile Asp Phe Gly Leu Asp Leu Gln Pro Cys Ile
            500                 505                 510

Asp Leu Ile Glu Lys Pro Ala Gly Pro Pro Gly Ile Leu Ala Leu Leu
        515                 520                 525

Asp Glu Glu Cys Trp Phe Pro Lys Ala Thr Asp Lys Ser Phe Val Glu
    530                 535                 540

Lys Val Met Gln Glu Gln Gly Thr His Pro Lys Phe Gln Lys Pro Lys
545                 550                 555                 560

Gln Leu Lys Asp Lys Ala Asp Phe Cys Ile Ile His Tyr Ala Gly Lys
                565                 570                 575

Val Asp Tyr Lys Ala Asp Glu Trp Leu Met Lys Asn Met Asp Pro Leu
            580                 585                 590

Asn Asp Asn Ile Ala Thr Leu Leu His Gln Ser Ser Asp Lys Phe Val
        595                 600                 605

Ser Glu Leu Trp Lys Asp Val Asp Arg Ile Ile Gly Leu Asp Gln Val
    610                 615                 620

Ala Gly Met Ser Glu Thr Ala Leu Pro Gly Ala Phe Lys Thr Arg Lys
625                 630                 635                 640

Gly Met Phe Arg Thr Val Gly Gln Leu Tyr Lys Glu Gln Leu Ala Lys
                645                 650                 655

Leu Met Ala Thr Leu Arg Asn Thr Asn Pro Asn Phe Val Arg Cys Ile
            660                 665                 670

Ile Pro Asn His Glu Lys Lys Ala Gly Lys Leu Asp Pro His Leu Val
        675                 680                 685

Leu Asp Gln Leu Arg Cys Asn Gly Val Leu Glu Gly Ile Arg Ile Cys
    690                 695                 700

Arg Gln Gly Phe Pro Asn Arg Val Val Phe Gln Glu Phe Arg Gln Arg
705                 710                 715                 720

Tyr Glu Ile Leu Thr Pro Asn Ser Ile Pro Lys Gly Phe Met Asp Gly
                725                 730                 735

Lys Gln Ala Cys Val Leu Met Ile Lys Ala Leu Glu Leu Asp Ser Asn
            740                 745                 750

Leu Tyr Arg Ile Gly Gln Ser Lys Val Phe Phe Arg Ala Gly Val Leu
        755                 760                 765

Ala His Leu Glu Glu Glu Arg Asp Leu Lys Ile Thr Asp Val Ile Ile
    770                 775                 780

Gly Phe Gln Ala Cys Cys Arg Gly Tyr Leu Ala Arg Lys Ala Phe Ala
785                 790                 795                 800

Lys Arg Gln Gln Gln Leu Thr Ala Met Lys Val Leu Gln Arg Asn Cys
                805                 810                 815

Ala Ala Tyr Leu Lys Leu Arg Asn Trp Gln Trp Trp Arg Leu Phe Thr
            820                 825                 830

Lys Val Lys Pro Leu Leu Gln Val Ser Arg Gln Glu Glu Met Met
        835                 840                 845

Ala Lys Glu Glu Glu Leu Val Lys Val Arg Glu Lys Gln Leu Ala Ala
    850                 855                 860

Glu Asn Arg Leu Thr Glu Met Glu Thr Leu Gln Ser Gln Leu Met Ala
865                 870                 875                 880

Glu Lys Leu Gln Leu Gln Glu Gln Leu Gln Ala Glu Thr Glu Leu Cys
                885                 890                 895

Ala Glu Ala Glu Glu Leu Arg Ala Arg Leu Thr Ala Lys Lys Gln Glu
            900                 905                 910
```

-continued

```
Leu Glu Glu Ile Cys His Asp Leu Glu Ala Arg Val Glu Glu Glu
        915                 920                 925

Glu Arg Cys Gln His Leu Gln Ala Glu Lys Lys Met Gln Gln Asn
    930                 935                 940

Ile Gln Glu Leu Glu Glu Gln Leu Glu Glu Glu Ser Ala Arg Gln
945                 950                 955                 960

Lys Leu Gln Leu Glu Lys Val Thr Thr Glu Ala Lys Leu Lys Leu
                965                 970                 975

Glu Glu Glu Gln Ile Ile Leu Glu Asp Gln Asn Cys Lys Leu Ala Lys
            980                 985                 990

Glu Lys Lys Leu Leu Glu Asp Arg Ile Ala Glu Phe Thr Thr Asn Leu
            995                 1000                1005

Thr Glu Glu Glu Lys Ser Lys Ser Leu Ala Lys Leu Lys Asn
    1010                1015                1020

Lys His Glu Ala Met Ile Thr Asp Leu Glu Glu Arg Leu Arg Arg
    1025                1030                1035

Glu Glu Lys Gln Arg Gln Glu Leu Glu Lys Thr Arg Arg Lys Leu
    1040                1045                1050

Glu Gly Asp Ser Thr Asp Leu Ser Asp Gln Ile Ala Glu Leu Gln
    1055                1060                1065

Ala Gln Ile Ala Glu Leu Lys Met Gln Leu Ala Lys Lys Glu Glu
    1070                1075                1080

Glu Leu Gln Ala Ala Leu Ala Arg Val Glu Glu Ala Ala Gln
    1085                1090                1095

Lys Asn Met Ala Leu Lys Lys Ile Arg Glu Leu Glu Ser Gln Ile
    1100                1105                1110

Ser Glu Leu Gln Glu Asp Leu Glu Ser Glu Arg Ala Ser Arg Asn
    1115                1120                1125

Lys Ala Glu Lys Gln Lys Arg Asp Leu Gly Glu Glu Leu Glu Ala
    1130                1135                1140

Leu Lys Thr Glu Leu Glu Asp Thr Leu Asp Ser Thr Ala Ala Gln
    1145                1150                1155

Gln Glu Leu Arg Ser Lys Arg Glu Gln Glu Val Asn Ile Leu Lys
    1160                1165                1170

Lys Thr Leu Glu Glu Glu Ala Lys Thr His Glu Ala Gln Ile Gln
    1175                1180                1185

Glu Met Arg Gln Lys His Ser Gln Ala Val Glu Glu Leu Ala Glu
    1190                1195                1200

Gln Leu Glu Gln Thr Lys Arg Val Lys Ala Asn Leu Glu Lys Ala
    1205                1210                1215

Lys Gln Thr Leu Glu Asn Glu Arg Gly Glu Leu Ala Asn Glu Val
    1220                1225                1230

Lys Val Leu Leu Gln Gly Lys Gly Asp Ser Glu His Lys Arg Lys
    1235                1240                1245

Lys Val Glu Ala Gln Leu Gln Glu Leu Gln Val Lys Phe Asn Glu
    1250                1255                1260

Gly Glu Arg Val Arg Thr Glu Leu Ala Asp Lys Val Thr Lys Leu
    1265                1270                1275

Gln Val Glu Leu Asp Asn Val Thr Gly Leu Leu Ser Gln Ser Asp
    1280                1285                1290

Ser Lys Ser Ser Lys Leu Thr Lys Asp Phe Ser Ala Leu Glu Ser
    1295                1300                1305

Gln Leu Gln Asp Thr Gln Glu Leu Leu Gln Glu Glu Asn Arg Gln
    1310                1315                1320
```

```
Lys Leu Ser Leu Ser Thr Lys Leu Lys Gln Val Glu Asp Glu Lys
1325                1330                1335

Asn Ser Phe Arg Glu Gln Leu Glu Glu Glu Glu Ala Lys His
1340                1345                1350

Asn Leu Glu Lys Gln Ile Ala Thr Leu His Ala Gln Val Ala Asp
1355                1360                1365

Met Lys Lys Lys Met Glu Asp Ser Val Gly Cys Leu Glu Thr Ala
1370                1375                1380

Glu Glu Val Lys Arg Lys Leu Gln Lys Asp Leu Glu Gly Leu Ser
1385                1390                1395

Gln Arg His Glu Glu Lys Val Ala Ala Tyr Asp Lys Leu Glu Lys
1400                1405                1410

Thr Lys Thr Arg Leu Gln Gln Glu Leu Asp Asp Leu Leu Val Asp
1415                1420                1425

Leu Asp His Gln Arg Gln Ser Ala Cys Asn Leu Glu Lys Lys Gln
1430                1435                1440

Lys Lys Phe Asp Gln Leu Leu Ala Glu Glu Lys Thr Ile Ser Ala
1445                1450                1455

Lys Tyr Ala Glu Glu Arg Asp Arg Ala Glu Ala Glu Ala Arg Glu
1460                1465                1470

Lys Glu Thr Lys Ala Leu Ser Leu Ala Arg Ala Leu Glu Glu Ala
1475                1480                1485

Met Glu Gln Lys Ala Glu Leu Glu Arg Leu Asn Lys Gln Phe Arg
1490                1495                1500

Thr Glu Met Glu Asp Leu Met Ser Ser Lys Asp Asp Val Gly Lys
1505                1510                1515

Ser Val His Glu Leu Glu Lys Ser Lys Arg Ala Leu Glu Gln Gln
1520                1525                1530

Val Glu Glu Met Lys Thr Gln Leu Glu Glu Leu Glu Asp Glu Leu
1535                1540                1545

Gln Ala Thr Glu Asp Ala Lys Leu Arg Leu Glu Val Asn Leu Gln
1550                1555                1560

Ala Met Lys Ala Gln Phe Glu Arg Asp Leu Gln Gly Arg Asp Glu
1565                1570                1575

Gln Ser Glu Glu Lys Lys Lys Gln Leu Val Arg Gln Val Arg Glu
1580                1585                1590

Met Glu Ala Glu Leu Glu Asp Glu Arg Lys Gln Arg Ser Met Ala
1595                1600                1605

Val Ala Ala Arg Lys Lys Leu Glu Met Asp Leu Lys Asp Leu Glu
1610                1615                1620

Ala His Ile Asp Ser Ala Asn Lys Asn Arg Asp Glu Ala Ile Lys
1625                1630                1635

Gln Leu Arg Lys Leu Gln Ala Gln Met Lys Asp Cys Met Arg Glu
1640                1645                1650

Leu Asp Asp Thr Arg Ala Ser Arg Glu Glu Ile Leu Ala Gln Ala
1655                1660                1665

Lys Glu Asn Glu Lys Lys Leu Lys Ser Met Glu Ala Glu Met Ile
1670                1675                1680

Gln Leu Gln Glu Glu Leu Ala Ala Ala Glu Arg Ala Lys Arg Gln
1685                1690                1695

Ala Gln Gln Glu Arg Asp Glu Leu Ala Asp Glu Ile Ala Asn Ser
1700                1705                1710

Ser Gly Lys Gly Ala Leu Ala Leu Glu Glu Lys Arg Arg Leu Glu
1715                1720                1725
```

-continued

| | | | | | | | | | | | |
|---|---|---|---|---|---|---|---|---|---|---|---|
| Ala | Arg | Ile | Ala | Gln | Leu | Glu | Glu | Leu | Glu | Glu | Gln | Gly |
| | 1730 | | | | 1735 | | | | 1740 | | |
| Asn | Thr | Glu | Leu | Ile | Asn | Asp | Arg | Leu | Lys | Lys | Ala | Asn | Leu | Gln |
| | 1745 | | | | 1750 | | | | 1755 | | |
| Ile | Asp | Gln | Ile | Asn | Thr | Asp | Leu | Asn | Leu | Glu | Arg | Ser | His | Ala |
| | 1760 | | | | 1765 | | | | 1770 | | |
| Gln | Lys | Asn | Glu | Asn | Ala | Arg | Gln | Gln | Leu | Glu | Arg | Gln | Asn | Lys |
| | 1775 | | | | 1780 | | | | 1785 | | |
| Glu | Leu | Lys | Val | Lys | Leu | Gln | Glu | Met | Glu | Gly | Thr | Val | Lys | Ser |
| | 1790 | | | | 1795 | | | | 1800 | | |
| Lys | Tyr | Lys | Ala | Ser | Ile | Thr | Ala | Leu | Glu | Ala | Lys | Ile | Ala | Gln |
| | 1805 | | | | 1810 | | | | 1815 | | |
| Leu | Glu | Glu | Gln | Leu | Asp | Asn | Glu | Thr | Lys | Glu | Arg | Gln | Ala | Ala |
| | 1820 | | | | 1825 | | | | 1830 | | |
| Cys | Lys | Gln | Val | Arg | Arg | Thr | Glu | Lys | Lys | Leu | Lys | Asp | Val | Leu |
| | 1835 | | | | 1840 | | | | 1845 | | |
| Leu | Gln | Val | Asp | Asp | Glu | Arg | Arg | Asn | Ala | Glu | Gln | Tyr | Lys | Asp |
| | 1850 | | | | 1855 | | | | 1860 | | |
| Gln | Ala | Asp | Lys | Ala | Ser | Thr | Arg | Leu | Lys | Gln | Leu | Lys | Arg | Gln |
| | 1865 | | | | 1870 | | | | 1875 | | |
| Leu | Glu | Glu | Ala | Glu | Glu | Glu | Ala | Gln | Arg | Ala | Asn | Ala | Ser | Arg |
| | 1880 | | | | 1885 | | | | 1890 | | |
| Arg | Lys | Leu | Gln | Arg | Glu | Leu | Glu | Asp | Ala | Thr | Glu | Thr | Ala | Asp |
| | 1895 | | | | 1900 | | | | 1905 | | |
| Ala | Met | Asn | Arg | Glu | Val | Ser | Ser | Leu | Lys | Asn | Lys | Leu | Arg | Arg |
| | 1910 | | | | 1915 | | | | 1920 | | |
| Gly | Asp | Leu | Pro | Phe | Val | Val | Pro | Arg | Arg | Met | Ala | Arg | Lys | Gly |
| | 1925 | | | | 1930 | | | | 1935 | | |
| Ala | Gly | Asp | Gly | Ser | Asp | Glu | Glu | Val | Asp | Gly | Lys | Ala | Asp | Gly |
| | 1940 | | | | 1945 | | | | 1950 | | |
| Ala | Glu | Ala | Lys | Pro | Ala | Glu | | | | | |
| | 1955 | | | | 1960 | | | | | | |

MYOSIN-IIA S1943 PHOSPHORYLATION AS A MARKER OF TUMOR INVASION

CROSS-REFERENCE TO RELATED APPLICATIONS

This application claims benefit of U.S. Provisional Application No. 61/453,336 filed Mar. 16, 2011, the contents of which are hereby incorporated by reference.

STATEMENT OF GOVERNMENT SUPPORT

This invention was made with government support under grant number CA100324 awarded by the National Cancer Institute. The government has certain rights in the invention.

SEQUENCE LISTING

The ".txt" Sequence Listing filed by EFS and which is entitled 96700_1802_ST25.txt, is 17 kilobytes in size and which was created on Feb. 3, 2012 is hereby incorporated by reference.

BACKGROUND OF THE INVENTION

Throughout this application various publications are referred to by number in parentheses. Full citations for these references may be found at the end of the specification. The disclosures of these publications are hereby incorporated by reference in their entirety into the subject application to more fully describe the art to which the subject invention pertains.

Although significant progress has been made in the molecular characterization of cancers, such as breast cancer, at present there are insufficient methodologies to predict risk for metastatic disease. Most biomarkers rely on correlating changes in overall protein levels with specific cancer-related biological processes; however, it is recognized that primary tumors, such as in breast cancer, exhibit alterations in signaling pathways that will affect post-translational modifications rather than elicit gross changes in protein expression levels. As a consequence, changes in post-translational modifications (e.g. phosphorylation) may be better predictors of disease.

The present invention addresses this need by providing a biomarker which is a predictor of metastasis and cancer prognosis.

SUMMARY OF THE INVENTION

A method is provided for determining if cells of a tumor in an organ or a tissue in a subject are likely to invade another organ or tissue in the subject comprising determining if a sample of the tumor, or a sample derived from the tumor, comprises a phosphorylated S1943 residue of a myosin-IIA heavy chain, wherein cells of the tumor are likely to invade another organ or tissue if the sample comprises the phosphorylated S1943 residue of a myosin-IIA heavy chain, and wherein absence of a phosphorylated S1943 residue of a myosin-IIA heavy chain does not indicate that cells of the tumor are likely to invade another organ or tissue.

A method is also provided for determining if a cancer is likely to metastasize comprising determining if a sample of the cancer, or a sample derived from the cancer, comprises a phosphorylated S1943 residue of a myosin-IIA heavy chain, wherein the cancer is likely to metastasize if the sample comprises the phosphorylated S1943 residue of a myosin-IIA heavy chain.

A kit is provided comprising a detectably-labeled antibody directed to phosphorylated S1943 residue of a myosin-IIA heavy chain, or a detectably-labeled fragment of an antibody which binds phosphorylated S1943 residue of a myosin-IIA heavy chain, and written instructions for using the detectably-labeled antibody or detectably-labeled fragment of an antibody to detect a phosphorylated S1943 residue of a myosin-IIA heavy chain in a sample.

DETAILED DESCRIPTION OF THE INVENTION

Figures 1A, 1B:
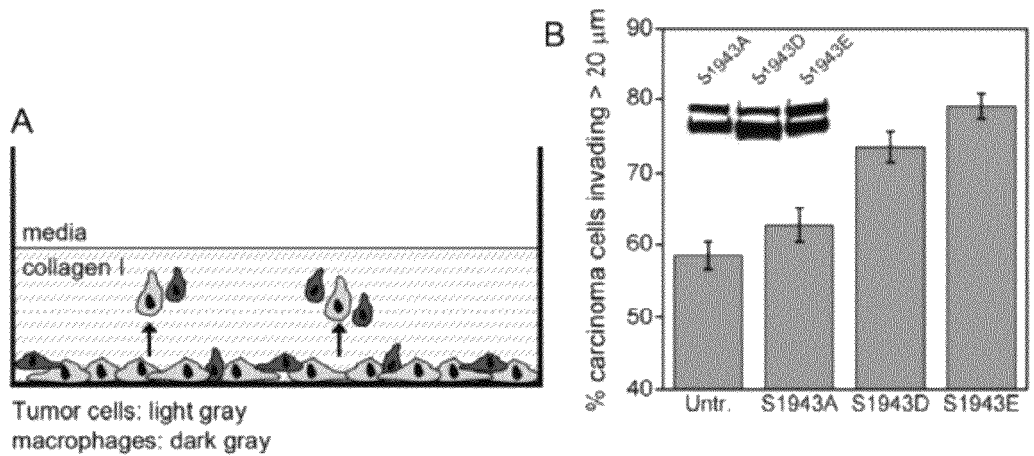
FIG. 1A-1B: 3D invasion assay. (1A) Cartoon of assay. Tumor cells and macrophages are plated on the bottom of a MatTek dish and overlaid with a collagen-I gel. After 24 hours, the proportion of cells invading the collagen is determined by confocal microscopy. (1B) Proportion of invasive MDA-MB-231 cells in the presence of macrophages (two independent experiments performed in duplicate). Inset: Blot showing endogenous non-muscle myosin heavy chain IIA (NMHC-IIA) (lower band) and GFP-NMHC-IIA mutant (upper band).

A method is provided for determining if cells of a tumor in an organ or a tissue in a subject are likely to invade another organ or tissue in the subject comprising determining if a sample of the tumor, or a sample derived from the tumor, comprises a phosphorylated S1943 residue of a myosin-IIA heavy chain, wherein cells of the tumor are likely to invade another organ or tissue if the sample comprises the phosphorylated S1943 residue of a myosin-IIA heavy chain, and wherein absence of a phosphorylated S1943 residue of a myosin-IIA heavy chain does not indicate that cells of the tumor are likely to invade another organ or tissue.

A method is provided for determining if a cancer is likely to metastasize comprising determining if a sample of the cancer, or a sample derived from the cancer, comprises a phosphorylated S1943 residue of a myosin-IIA heavy chain, wherein the cancer is likely to metastasize if the sample comprises the phosphorylated S1943 residue of a myosin-IIA heavy chain.

In an embodiment of the methods, determining if the sample of the tumor, or the sample derived from the tumor, or the sample of the cancer, or the sample derived from the cancer, comprises the phosphorylated S1943 residue of a myosin-IIA heavy chain comprises contacting the sample of the tumor, or the sample derived from the tumor, or the sample of the cancer, or the sample derived from the cancer, respectively, with a detectable agent which selectively binds to phosphorylated S1943 residue of a myosin-IIA heavy chain and detecting any bound detectable agent.

In an embodiment of the methods the tumor is a breast cancer tumor. In an embodiment of the methods the rumor is a tumor of the prostate, lung, liver, pancreas, kidney, ovary, testicle, utenis, glia, central nervous system, oesphagus, stomach, colon, or is a glioblastoma. In an embodiment of the methods, the tumor is a solid state tumor. In an embodiment, the tumor is a tumor of a solid tissue.

In an embodiment of the methods the detectable agent is an antibody or an antigen-binding fragment of an antibody. In an embodiment of the methods the antibody or the antigen-binding fragment of an antibody is labeled with a detectable label. In an embodiment, the detectable agent binds to the cell surface of a cell of the sample. In an embodiment, the sample is not a lysate.

In an embodiment of the methods the myosin-IIA is non-muscle myosin-IIA heavy chain.

In an embodiment of the methods the myosin-IIA heavy chain comprises consecutive amino acid residues having the sequence set forth in SEQ ID NO:1—

```
MAQQAADKYL YVDKNFINNP LAQADWAAKK LVWVPSDKSG FEPASLKEEV GEEAIVELVE
NGKKVKVNKD DIQKMNPPKF SKVEDMAELT CLNEASVLHN LKERYYSGLI YTYSGLFCVV
INPYKNLPIY SEEIVEMYKG KKRHEMPPHI YAITDTAYRS MMQDREDQSI LCTGESGAGK
TENTKKVIQY LAYVASSHKS KKDQGELERQ LLQANPILEA FGNAKTVKND NSSRFGKFIR
INFDVNGYIV GANIETYLLE KSRAIRQAKE ERTFHIFYYL LSGAGEHLKT DLLLEPYNKY
RFLSNGHVTI PGQQDKDMFQ ETMEAMRIMG IPEEEQMGLL RVISGVLQLG NIVFKKERNT
DQASMPDNTA AQKVSHLLGI NVTDFTRGIL TPRIKVGRDY VQKAQTKEQA DFAIEALAKA
TYERMFRWLV LRINKALDKT KRQGASFIGI LDIAGFEIFD LNSFEQLCIN YTNEKLQQLF
NHTMFILEQE EYQREGIEWN FIDFGLDLQP CIDLIEKPAG PPGILALLDE ECWFPKATDK
SFVEKVMQEQ GTHPKFQKPK QLKDKADFCI IHYAGKVDYK ADEWLMKNMD PLNDNIATLL
HQSSDKFVSE LWKDVDRIIG LDQVAGMSET ALPGAFKTRK GMFRTVGQLY KEQLAKLMAT
LRNTNPNFVR CIIPNHEKKA GKLDPHLVLD QLRCNGVLEG IRICRQGFPN RVVFQEFRQR
YEILTPNSIP KGFMDGKQAC VLMIKALELD SNLYRIGQSK VFFRAGVLAH LEEERDLKIT
DVIIGFQACC RGYLARKAFA KRQQQLTAMK VLQRNCAAYL KLRNWQWWRL FTKVKPLLQV
SRQEEEMMAK EEELVKVREK QLAAENRLTE METLQSQLMA EKLQLQEQLQ AETELCAEAE
ELRARLTAKK QELEEICHDL EARVEEEEER CQHLQAEKKK MQQNIQELEE QLEEEESARQ
KLQLEKVTTE AKLKKLEEEQ IILEDQNCKL AKEKELLEDR IAEFTTNLTE EEEKSKSLAK
LKNKHEAMIT DLEERLRREE KQRQELEKTR RKLEGDSTDL SDQIAELQAQ IAELKMQLAK
KEEELQAALA RVEEEAAQKN MALKKIRELE SQISELQEDL ESERASRNKA EKQKRDLGEE
LEALKTELED TLDSTAAQQE LRSKREQEVN ILKKTLEEEA KTHEAQIQEM RQKHSQAVEE
LAEQLEQTKR VKANLEKAKQ TLENERGELA NEVKVLLQGK GDSEHKRKKV EAQLQELQVK
FNEGERVRTE LADKVTKLQV ELDNVTGLLS QSDSKSSKLT KDFSALESQL QDTQELLQEE
NRQKLSLSTK LKQVEDEKNS FREQLEEEEE AKHNLEKQIA TLHAQVADMK KKMEDSVGCL
ETAEEVKRKL QKDLEGLSQR HEEKVAAYDK LEKTKTRLQQ ELDDLLVDLD HQRQSACNLE
KKQKKFDQLL AEEKTISAKY AEERDRAEAE AREKETKALS LARALEEAME QKAELERLNK
QFRTEMEDLM SSKDDVGKSV HELEKSKRAL EQQVEEMKTQ LEELEDELQA TEDAKLRLEV
NLQAMKAQFE RDLQGRDEQS EEKKKQLVRQ VREMEAELED ERKQRSMAVA ARKKLEMDLK
DLEAHIDSAN KNRDEAIKQL RKLQAQMKDC MRELDDTRAS REEILAQAKE NEKKLKSMEA
EMIQLQEELA AAERAKRQAQ QERDELADEI ANSSGKGALA LEEKRRLEAR IAQLEEELEE
EQGNTELIND RLKKANLQID QINTDLNLER SHAQKNENAR QQLERQNKEL KVKLQEMEGT
```

-continued

```
VKSKYKASIT ALEAKIAQLE EQLDNETKER QAACKQVRRT EKKLKDVLLQ VDDERRNAEQ

YKDQADKAST RLKQLKRQLE EAEEEAQRAN ASRRKLQREL EDATETADAM NREVSSLKNK

LRRGDLPFVV PRRMARKGAG DGSDEEVDGK ADGAEAKPAE
```

In an embodiment, the S1943 residue is the serine at residue number 1943 of SEQ ID NO:1.

Also provided is a method for determining if a cancer is likely to metastasize comprising determining if the cancer comprises a phosphorylated S1943 residue of a myosin-IIA heavy chain, wherein the cancer is likely to metastasize if the sample comprises the phosphorylated S1943 residue of a myosin-IIA heavy chain. In an embodiment, determining if the cancer comprises the phosphorylated S1943 residue of a myosin-IIA heavy chain comprises contacting the cancer with a detectable agent which selectively binds to phosphorylated S1943 residue of a myosin-IIA heavy chain and detecting any bound detectable agent. In an embodiment, the detectable agent is administered directly into the cancer, or is administered to the subject with the cancer. In an embodiment, the detectable agent is administered by injection or catheterization into the cancer. In an embodiment, the detectable agent is a detectably-labeled antibody directed to phosphorylated S1943 residue of a myosin-IIA heavy chain, or a detectably-labeled fragment of an antibody which binds phosphorylated S1943 residue of a myosin-IIA heavy chain. In an embodiment, the detectable label is fluorescent, is radioactive, or is radio-opaque.

Also provided is a kit comprising a detectably-labeled antibody directed to phosphorylated S1943 residue of a myosin-IIA heavy chain, or a detectably-labeled fragment of an antibody which binds phosphorylated S1943 residue of a myosin-IIA heavy chain, and written instructions for using the detectably-labeled antibody or detectably-labeled fragment of an antibody to detect a phosphorylated S1943 residue of a myosin-IIA heavy chain in a sample.

As used herein, the term "antibody" refers to complete, intact antibodies, "fragment of an antibody" refers to Fab, Fab', F(ab)₂, and other fragments thereof which fragments bind the antigen of interest, in this case phosphorylated S1943 of nonmuscle myosin-IIA heavy chain (Myh9). Complete, intact antibodies include, but are not limited to, monoclonal antibodies such as murine monoclonal antibodies, polyclonal antibodies, chimeric antibodies, human antibodies, and humanized antibodies.

Various forms of antibodies may be produced using standard recombinant DNA techniques (see 24). For example, "chimeric" antibodies may be constructed, in which the antigen binding domain from an animal antibody is linked to a human constant domain (an antibody derived initially from a nonhuman mammal in which recombinant DNA technology has been used to replace all or part of the hinge and constant regions of the heavy chain and/or the constant region of the light chain, with corresponding regions from a human immunoglobulin light chain or heavy chain) (see, e.g., 25 & 26). Chimeric antibodies reduce the immunogenic responses elicited by animal antibodies when used in human clinical treatments. In addition, recombinant "humanized" antibodies may be synthesized. Humanized antibodies are antibodies initially derived from a nonhuman mammal in which recombinant DNA technology has been used to substitute some or all of the amino acids not required for antigen binding with amino acids from corresponding regions of a human immunoglobulin light or heavy chain. That is, they are chimeras comprising mostly human immunoglobulin sequences into which the regions responsible for specific antigen-binding have been inserted (see, e.g., PCT patent application WO 94/04679). Animals are immunized with the desired antigen, the corresponding antibodies are isolated and the portion of the variable region sequences, responsible for specific antigen binding are removed. The animal-derived antigen binding regions are then cloned into the appropriate position of the human antibody genes in which the antigen binding regions have been deleted. Humanized antibodies minimize the use of heterologous (inter-species) sequences in antibodies for use in human therapies, and are less likely to elicit unwanted immune responses. Primatized antibodies can be produced similarly.

Another embodiment of the antibodies employed in the compositions and methods of the invention is a human antibody, which can be produced in nonhuman animals, such as transgenic animals harboring one or more human immunoglobulin transgenes. Such animals may be used as a source for splenocytes for producing hybridomas, for example as is described in U.S. Pat. No. 5,569,825.

Antibody fragments and univalent antibodies may also be used in the methods and compositions of this invention. Univalent antibodies comprise a heavy chain/light chain dimer bound to the Fc (or stem) region of a second heavy chain. "Fab region" refers to those portions of the chains which are roughly equivalent, or analogous, to the sequences which comprise the Y branch portions of the heavy chain and to the light chain in its entirety, and which collectively (in aggregates) have been shown to exhibit antibody activity. A Fab protein includes aggregates of one heavy and one light chain (commonly known as Fab'), as well as tetramers which correspond to the two branch segments of the antibody Y, (commonly known as F(ab)₂), whether any of the above are covalently or non-covalently aggregated, so long as the aggregation is capable of specifically reacting with a particular antigen or antigen family.

As used herein, an agent that "selectively binds to phosphorylated S1943 residue of a myosin-IIA heavy chain", or grammatical equivalent, means an agent which binds to myosin-IIA comprising a phosphorylated S1943 residue ("pS1943") but which does not bind myosin-IIA having no phosphorylated S1943 residue. In non-limiting examples the agent is an antibody, or fragment of an antibody. In a preferred embodiment, the agent that selectively binds to phosphorylated S1943 residue of a myosin-IIA heavy chain does not bind to any other cellular component.

As used herein, a "cancer" is a disease state characterized by the presence in a subject of cells demonstrating abnormal uncontrolled replication. As used herein a "tumor" is a detectable malignant tumor usually presenting as a lesion or lump located in an organ or tissue in a subject, and may also be present in adjacent organs and or tissues in a subject.

As used herein "metastasize" means, in regard to a cancer or tumor, to spread from one organ or tissue of a subject to another non-adjacent organ or tissue of the subject.

As used herein, a "detectable agent" is any agent that binds to myosin-IIA heavy chain comprising a phosphorylated S1943 residue and which can be detected or observed, when bound, by methods known in the art. In non-limiting examples, the detectable agent can be an antibody or a fragment of an antibody, which is itself detectable, e.g. by a secondary antibody, or which is labeled with a detectable marker such as a radioisotope, a fluorophore, a dye etc. permitting detection of the presence of the bound agent by the appropriate machine, or optionally in the case of visually detectable agents, with the human eye. In an embodiment, the amount of detected agent can be quantified.

As used herein, a "sample" of a cancer or of a tumor is a portion of the cancer or of the tumor, respectively, for example as obtained by a biopsy. As used herein a "sample derived from a tumor" is a sample of the tumor or of the cancer which has been treated chemically and/or mechanically, but in such a manner not to remove any phosphorylated S1943 residue of a myosin-IIA heavy chain which might be contained therein and in such a manner not to phosphorylate an S1943 residue of a myosin-IIA heavy chain which was non-phosphorylated prior to such chemical and/or mechanical treatment.

As used herein "likely to" in regard to describing an occurrence means more likely to occur than not to occur. (90% or more of cancer deaths result from metastases (see 2010 Cancer Facts & Figures, American Cancer Society. Cancer Facts & Figures is an annual publication of the American Cancer Society, Atlanta, Ga.)).

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Nonmuscle myosin-II is a hexameric complex comprised of two heavy chains (NMHC-II), two essential light chains and two regulatory light chains (1). Each heavy chain contains an N-terminal globular head containing the ATP and actin binding domains needed for motor activity, an intermediate coiled-coil domain and a C-terminal tailpiece. The S1943 phosphorylation site is located on the C-terminal tailpiece. The three NMHC-II isoforms (A, B, and C) exhibit distinct patterns of tissue and cell expression (2), have different enzymatic activities (3-5), interact with different proteins (6-8), and have unique functional roles in vivo (9-14). More importantly, myosin-II regulates and integrates multiple steps in the motility cycle of cells, including cell polarization and protrusion, and the assembly and turnover of adhesions (15, 16). In animal models, myosin-II regulatory pathways are activated in invasive breast cancer cells (17), and myosin-II activity is required for matrix deformation and breast cancer cell motility through a three-dimensional matrix (18). These observations suggest that myosin-II-based contractility is a critical component of carcinoma invasion.

Regulatory light chain phosphorylation is a well-established mechanism for activation of the myosin-II motor (19). However, there is emerging evidence from this laboratory, and others, that heavy chain phosphorylation, which promotes myosin-II filament disassembly (20, 21), provides another regulatory control for modifying myosin-II activity. Studies from this laboratory showed that EGF stimulation of human breast cancer cells induces rapid and reversible phosphorylation on S1943 of NMHC-IIA (22), which can be phosphorylated in vitro by CK2. Moreover, it was shown that expression of NMHC-IIA phosphomimetics (S1943E/D) enhances the EGF-stimulated chemotactic motility of breast cancer cells (22).

Results and Discussion

Using a previously-developed in vitro 3-D invasion assay that reconstitutes macrophage-dependent invasion of tumor cells into a collagen gel (see 23 for assay) it was observed that breast tumor cells expressing GFP-NMHC-IIA S1943E, a NMHC-IIA phosphomimetic, exhibited a 25% increase in invasion as compared to untransfected cells (p value <0.00001) (FIG. 1). The 3-D invasion assay results indicate the usefulness of phosphorylation status of NMHC-IIA S1943E as a metastatic marker and are significant finding because more-limited 2-D assay results are not reliably predictive of in vivo metastatic behavior.

Figures 2A, 2B:
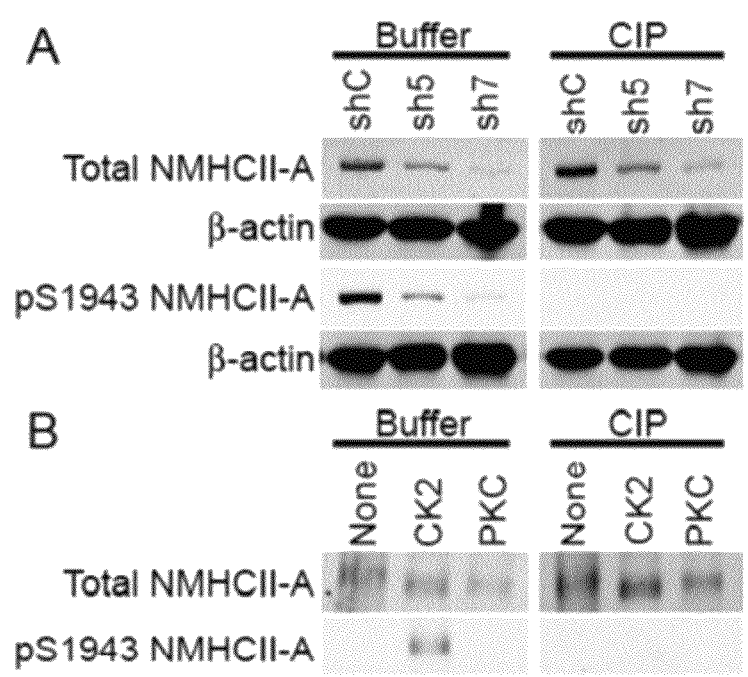
FIG. 2A-2B: Development of antibodies that specifically react with the NMHC-IIA pS1943. (2A) pS1943 antibodies react specifically with a MDA-MB-231 whole cell extract and CK2-phosphorylated NMHC-IIA rods, but not with muscle myosin heavy chain IIA (NMHC-IIB) rods (data not shown), unphosphorylated NMHC-IIA rods, or PKC-phosphorylated NMHC-IIA rods. (2B) Treatment with calf-intestine phosphatase (CIP), decreased the reactivity of the phospho-antibody with the MDA-MB-231 extract and NMHC-IIA CK2 phosphorylated rods.

Antibodies that recognize the myosin-IIA S1943 phosphorylation site were developed. Analyses demonstrated that the antibody recognizes a single band in a MDA-MB-231 breast tumor cell lysate, and that reactivity is reduced following snRNA-mediated knockdown of myosin-IIA and is abolished following treatment with calf intestinal phosphatase (FIG. 2A). In addition, the antibody recognized CK2-phosphorylated myosin-IIA rods (phosphorylation on S1943), but not PKC-phosphorylated rods (phosphorylation on S1916) or unphosphorylated myosin-IIA rods (FIG. 2B).

Figure 3:
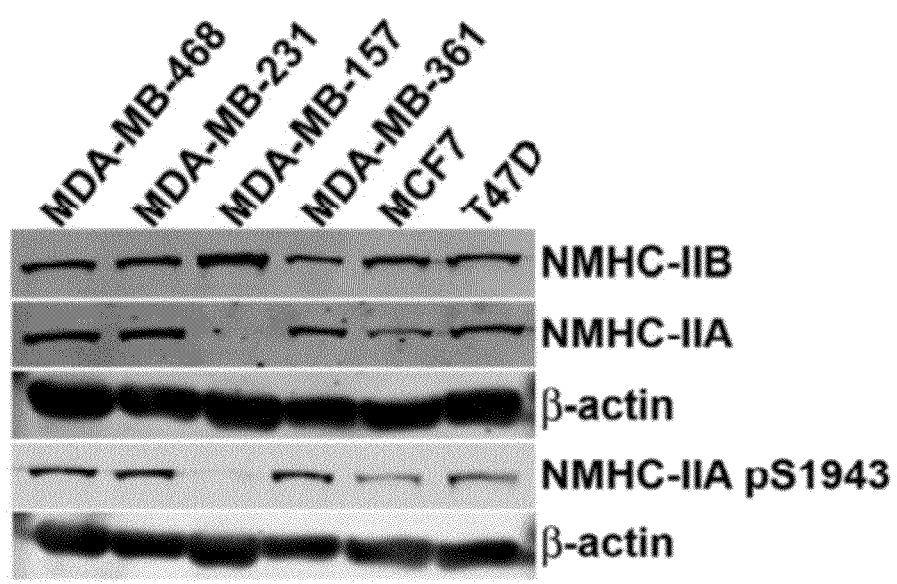
FIG. 3: Myosin-IIA heavy chain phosphorylation is detected in multiple human breast carcinoma cells lines.
Figure 4:
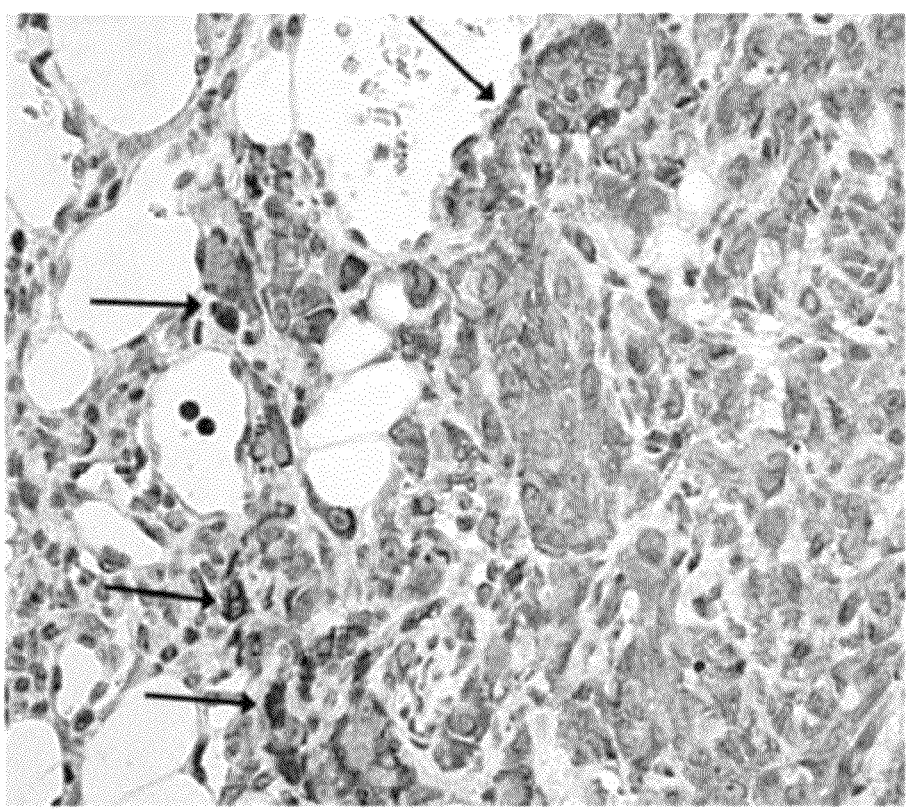
FIG. 4: MDA-MB-231 tumor. Arrows indicate localization of pS1943 NMHC-IIA in cells at the invasive edge of the tumor.

Myosin-IIA heavy chain phosphorylation is detected in multiple human breast carcinoma cells lines (FIG. 3). Moreover, immunohistochemical analysis of MDA-MB-231 late stage orthotopic tumors demonstrated that S1943-phosphorylated myosin-IIA localizes to the invasive edge of MDA-MB-231 tumors (FIG. 4).

Figures 5A, 5B:
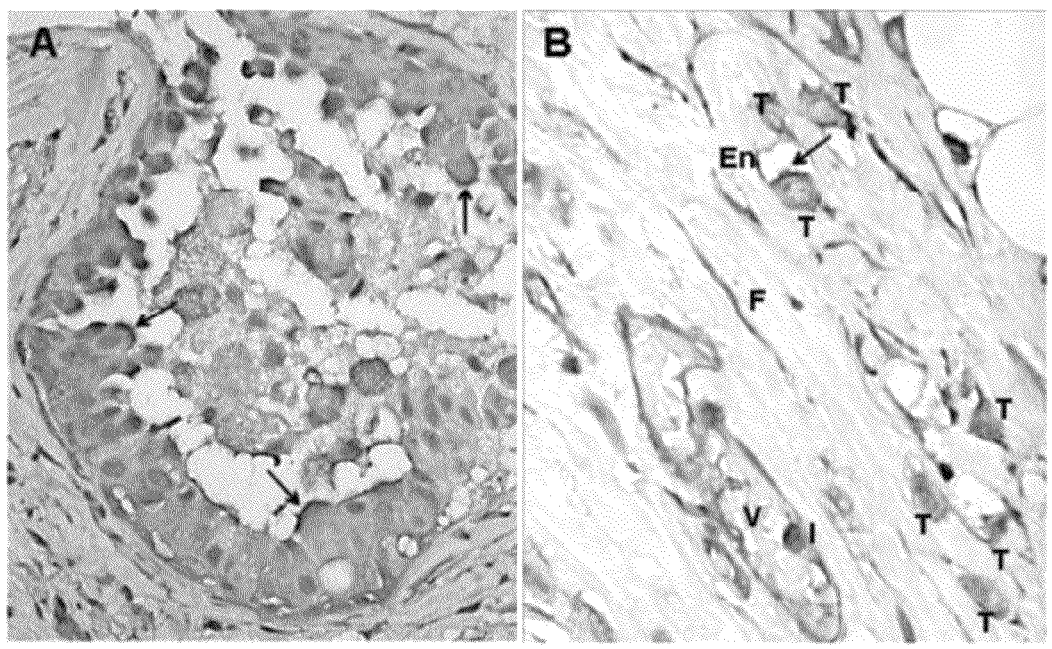
FIGS. 5A & 5B. NMHC-IIA pS1943 immunohistochemistry of human breast tumor samples. (5A) Intraductal carcinoma forming a central lumen. Arrows indicate intense pS1943 NMHC-IIA localization at the cell apex. (5B) High grade carcinoma at the invasive margin. Individual tumor cells (T) have spread into the adjacent connective tissue. The arrow shows a tumor cell that has moved into a lymphatic vessel, which was identified by its flattened endothelial cell nucleus (En). There is intense staining of the tumor cell edge facing the lumen, with delicate processes extending into the luminal space. In addition to expression in tumor cells, the endothelium of a small blood vessel (V), a marginated inflammatory cell (I) and stromal fibroblasts (F) are positive.

Immunohistochemistry of human breast tumors with the pS1943 antibody showed that phosphorylated myosin-IIA selectively localizes to the free cell surfaces of breast cancer cells. Intense apical staining of the cells facing the lumen of a high grade intraductal carcinoma was observed in situ (FIG. 5A). In addition, in a lobular carcinoma exhibiting invasion of the surrounding stroma and lymphatic spread, invasive tumor cells at the tumor margin selectively expressed myosin-IIA at the cell periphery. When cells had penetrated intracellular spaces, such as the lumen of a lymphatic channel, the localization was confined to the leading edge of the cell (FIG. 5B). These observations are significant because they show that in actual human breast tumors, and not just in breast cancer cell lines which may or may not accurately reflect the in situ situation, myosin-IIA heavy chain phosphorylation is associated with tumor cell invasion.

In summary, the studies demonstrated that S1943 phosphorylation on the myosin-IIA heavy chain enhances breast tumor motility invasion, and is associated with invasive cells in human breast tumor samples. Since the regulation of actomyosin contractility is critical for tumor cell migration and invasion, myosin-IIA S1943 phosphorylation serves as a prognostic indicator in human breast cancer.

REFERENCES

1. Bresnick, A. R. (1999) Molecular mechanisms of nonmuscle myosin-II regulation., Curr Opin Cell Biol 11, 26-33.
2. Golomb, E., Ma, X., Jana, S. S., Preston, Y. A., Kawamoto, S., Shoham, N. G., Goldin, E., Conti, M. A., Sellers, J. R., and Adelstein, R. S. (2004) Identification and characterization of nomnuscle myosin II-C, a new member of the myosin II family, J Biol Chem 279, 2800-2808.
3. Kovacs, M., Wang, F., Hu, A., Zhang, Y., and Sellers, J. R. (2003) Functional divergence of human cytoplasmic myo- 4. Rosenfeld, S. S., Xing, J., Chen, L. Q., and Sweeney, H. L. (2003) Myosin IIb is unconventionally conventional, *J Biol Chem* 278, 27449-27455.
5. Wang, F., Kovacs, M., Hu, A., Limouze, J., Harvey, E. V., and Sellers, J. R. (2003) Kinetic mechanism of non-muscle myosin IIB: functional adaptations for tension generation and maintenance, *J Biol Chem* 278, 27439-27448.
6. Kriajevska, M. V., Cardenas, M. N., Grigorian, M. S., Ambartsumian, N. S., Georgiev, G. P., and Lukanidin, E. M. (1994) Non-muscle myosin heavy chain as a possible target for protein encoded by metastasis-related mts-1 gene., *J Biol Chem* 269, 19679-19682.
7. Huang, H., Paliouras, M., Rambaldi, I., Lasko, P., and Featherstone, M. (2003) Nonmuscle myosin promotes cytoplasmic localization of PBX, *Mol Cell Biol* 23, 3636-3645.
8. Clark, K., Langeslag, M., van Leeuwen, B., Ran, L., Ryazanov, A. G., Figdor, C. G., Moolenaar, W. H., Jalink, K., and van Leeuwen, F. N. (2006) TRPM7, a novel regulator of actomyosin contractility and cell adhesion, *Embo J* 25, 290-301.
9. Tullio, A. N., Accili, D., Ferrans, V. J., Yu, Z. X., Takeda, K., Grinberg, A., Westphal, H., Preston, Y. A., and Adelstein, R. S. (1997) Nonmuscle myosin II-B is required for normal development of the mouse heart, *Proc Natl Acad Sci USA* 94, 12407-12412.
10. Lo, C. M., Buxton, D. B., Chua, G. C., Dembo, M., Adelstein, R. S., and Wang, Y. L. (2004) Nonmuscle myosin IIb is involved in the guidance of fibroblast migration, *Mol Biol Cell* 15, 982-989.
11. Meshel, A. S., Wei, Q., Adelstein, R. S., and Sheetz, M. P. (2005) Basic mechanism of three-dimensional collagen fibre transport by fibroblasts, *Nat Cell Biol* 7, 157-164.
12. Jana, S. S., Kawamoto, S., and Adelstein, R. S. (2006) A specific isoform of nonmuscle myosin II-C is required for cytokinesis in a tumor cell line, *J Biol Chem* 281, 24662-24670.
13. Conti, M. A., Even-Ram, S., Liu, C., Yamada, K. M., and Adelstein, R. S. (2004) Defects in cell adhesion and the visceral endoderm following ablation of nonmuscle myosin heavy chain II-A in mice, *J Biol Chem* 279, 41263-41266.
14. Cai, Y., Biais, N., Giannone, G., Tanase, M., Jiang, G., Hofman, J. M., Wiggins, C. H., Silberzan, P., Buguin, A., Ladoux, B., and Sheetz, M. P. (2006) Nonmuscle Myosin IIA-Dependent Force Inhibits Cell Spreading and Drives F-Actin Flow, *Biophys J* 91, 3907-3920.
15. Vicente-Manzanares, M., Zareno, J., Whitmore, L., Choi, C. K., and Horwitz, A. F. (2007) Regulation of protrusion, adhesion dynamics, and polarity by myosins IIA and IIB in migrating cells, *J Cell Biol* 176, 573-580.
16. Giannone, G., Dubin-Thaler, B. J., Rossier, O., Cai, Y., Chaga, O., Jiang, G., Beaver, W., Dobereiner, H. G., Freund, Y., Borisy, G., and Sheetz, M. P. (2007) Lamellipodial actin mechanically links myosin activity with adhesion-site formation, *Cell* 128, 561-575.
17. Wang, W., Wyckoff, J. B., Goswami, S., Wang, Y., Sidani, M., Segall, J. E., and Condeelis, J. S. (2007) Coordinated regulation of pathways for enhanced cell motility and chemotaxis is conserved in rat and mouse mammary tumors, *Cancer Res* 67, 3505-3511.
18. Wyckoff, J. B., Pinner, S. E., Gschmeissner, S., Condeelis, J. S., and Sahai, E. (2006) ROCK- and myosin-dependent matrix deformation enables protease-independent tumor-cell invasion in vivo, *Curr Biol* 16, 1515-1523.
19. Scholey, J. M., Taylor, K. A., and Kendrick-Jones, J. (1980) Regulation of non-muscle myosin assembly by calmodulin-dependent light chain kinase, *Nature* 287, 233-235.
20. Dulyaninova, N. G., Malashkevich, V. N., Almo, S. C., and Bresnick, A. R. (2005) Regulation of myosin-IIA assembly and Mts1 binding by heavy chain phosphorylation, *Biochemistry* 44, 6867-6876.
21. Murakami, N., Chauhan, V. P., and Elzing a, M. (1998) Two nonmuscle myosin II heavy chain isoforms expressed in rabbit brains: filament forming properties, the effects of phosphorylation by protein kinase C and casein kinase II, and location of the phosphorylation sites., *Biochemistry* 37, 1989-2003.
22. Dulyaninova, N. G., House, R. P., Betapudi, V., and Bresnick, A. R. (2007) Myosin-IIA heavy-chain phosphorylation regulates the motility of MDA-MB-231 carcinoma cells., *Mol Biol Cell* 18, 3144-3155.
23. Goswami, S., Sahai, E., Wyckoff, J. B., Cammer, M., Cox, D., Pixley, F. J., Stanley, E. R., Segall, J. E., and Condeelis, J. S. (2005) Macrophages promote the invasion of breast carcinoma cells via a colony-stimulating factor-1/epidermal growth factor paracrine loop, *Cancer Res* 65, 5278-5283.
24. Winter and Milstein, Nature 349: 293-99, 1991.
25. Cabilly et al., U.S. Pat. No. 4,816,567.
26. Morrison et al., Proc. Natl. Acad. Sci. 81: 6851-55, 1984.

What is claimed is:

1. A method for determining if cells of a tumor in an organ or in a tissue in a subject, are likely to invade another organ or tissue in the subject comprising determining if a sample of the tumor, or a sample obtained from the tumor, comprises human myosin-IIA heavy chain phosphorylated at residue S1943, comprising contacting the sample of the tumor, or the sample obtained from the tumor, with a detectable agent which comprises an antibody or an antigen-binding fragment of an antibody, which selectively binds to phosphorylated S1943 residue of human myosin-IIA heavy chain and detecting any bound detectable agent,
   wherein cells of the tumor are likely to invade another organ or tissue if the sample comprises the phosphorylated S1943 residue of human myosin-IIA heavy chain, and wherein absence of a phosphorylated S1943 residue of human myosin-IIA heavy chain does not indicate that cells of the tumor are likely to invade another organ or tissue.

2. The method of claim 1, wherein the human myosin-IIA heavy chain comprises SEQ ID NO:1.

3. The method of claim 1, wherein the detectable agent is an antibody.

4. The method of claim 3, wherein the antibody is labeled with a detectable label.

5. The method of claim 4, wherein the detectable label is fluorescent, is radioactive, or is radio-opaque.

6. The method of claim 1, wherein the phosphorylated S1943 residue of the human myosin-IIA heavy chain is detected on the surface of a cell of the sample.

7. The method of claim 1, wherein the sample obtained from the tumor is not a lysate.

8. The method of claim 1, wherein the tumor is a breast cancer tumor.

9. A method for determining if a cancer is likely to metastasize comprising determining if a sample of the cancer, or a sample obtained from the cancer, comprises human myosin-IIA heavy chain phosphorylated at residue S1943 comprising contacting the sample of the cancer, or the sample obtained from the cancer, with a detectable agent which comprises an antibody or an antigen-binding fragment of an antibody which selectively binds to phosphorylated S1943 residue of myosin-IIA heavy chain and detecting any bound detectable agent,
   wherein the cancer is likely to metastasize if the sample comprises the phosphorylated S1943 residue of human myosin-IIA heavy chain.

* * * * *

UNITED STATES PATENT AND TRADEMARK OFFICE
CERTIFICATE OF CORRECTION

| | | |
|---|---|---|
| PATENT NO. | : 8,541,181 B2 | Page 1 of 1 |
| APPLICATION NO. | : 13/419805 | |
| DATED | : September 24, 2013 | |
| INVENTOR(S) | : Anne Reba Bresnick | |

It is certified that error appears in the above-identified patent and that said Letters Patent is hereby corrected as shown below:

Column 1, lines 11-15, should read:

-- STATEMENT OF GOVERNMENT SUPPORT

This invention was made with government support under grant number CA 100324 awarded by the National Institutes of Health. The government has certain rights in the invention. --

Signed and Sealed this
Third Day of November, 2015

Michelle K. Lee
*Director of the United States Patent and Trademark Office*